(12) United States Patent
Vogt et al.

(10) Patent No.: US 8,967,142 B2
(45) Date of Patent: Mar. 3, 2015

(54) SYSTEM FOR PROVIDING EMERGENCY OXYGEN AND THERAPEUTIC OXYGEN

(75) Inventors: Thomas Vogt, Hamburg (DE); Andreas Westphal, Eutin (DE); Detlev Degenhardt, Stockelsdorf (DE)

(73) Assignee: Airbus Operations GmbH (DE)

( * ) Notice: Subject to any disclaimer, the term of this patent is extended or adjusted under 35 U.S.C. 154(b) by 595 days.

(21) Appl. No.: 12/682,403

(22) PCT Filed: Sep. 24, 2008

(86) PCT No.: PCT/EP2008/062774
§ 371 (c)(1),
(2), (4) Date: May 11, 2010

(87) PCT Pub. No.: WO2009/050006
PCT Pub. Date: Apr. 23, 2009

(65) Prior Publication Data
US 2010/0229864 A1 Sep. 16, 2010

Related U.S. Application Data

(60) Provisional application No. 60/998,781, filed on Oct. 12, 2007.

(30) Foreign Application Priority Data
Oct. 12, 2007 (DE) .......................... 10 2007 048 924

(51) Int. Cl.
A61M 16/00 (2006.01)
A62B 7/14 (2006.01)
A61M 16/10 (2006.01)
B64D 10/00 (2006.01)

(52) U.S. Cl.
CPC .................. *A62B 7/14* (2013.01); *A61M 16/10* (2013.01); *B64D 10/00* (2013.01); *A61M 2202/0208* (2013.01); *A61M 2205/84* (2013.01)
USPC ............... 128/204.18; 128/204.21; 244/118.5

(58) Field of Classification Search
USPC ........................................................ 244/118.5
See application file for complete search history.

(56) References Cited

U.S. PATENT DOCUMENTS

| 3,016,061 A | 1/1962 | Maddock |
| 3,045,691 A | 7/1962 | Young |
| 3,103,927 A * | 9/1963 | Henneman et al. ...... 128/201.28 |

(Continued)

FOREIGN PATENT DOCUMENTS

| DE | 10340985 A1 | 3/2005 |
| EP | 1512433 A2 | 3/2005 |

(Continued)

*Primary Examiner* — Loan H Thanh
*Assistant Examiner* — Andrew S Lo
(74) *Attorney, Agent, or Firm* — Lerner, David, Littenberg, Krumholz & Mentlik, LLP (57) ABSTRACT

The invention relates to a system for providing emergency oxygen and therapeutic oxygen in an aircraft, said system having an oxygen source, an oxygen conduction system comprising a second oxygen outlet, a device for providing emergency oxygen comprising a second oxygen inlet, a device for providing therapeutic oxygen, having a first oxygen inlet and a first oxygen outlet. According to the invention, the second oxygen outlet can be coupled to the first oxygen inlet, the first oxygen outlet can be coupled to the second oxygen inlet and the second oxygen outlet can be coupled to the second oxygen inlet.

10 Claims, 3 Drawing Sheets

(56) References Cited

U.S. PATENT DOCUMENTS

| | | | |
|---|---|---|---|
| 4,651,728 A | 3/1987 | Gupta et al. | |
| 5,199,423 A * | 4/1993 | Harral et al. | 128/202.26 |
| 5,357,949 A | 10/1994 | Bertheau et al. | |
| 5,531,807 A | 7/1996 | McCombs | |
| 2003/0233936 A1 | 12/2003 | Crome | |
| 2005/0061915 A1 | 3/2005 | Vogt et al. | |
| 2006/0032155 A1 | 2/2006 | Thomassin et al. | |

FOREIGN PATENT DOCUMENTS

| | | |
|---|---|---|
| EP | 1619120 A1 | 1/2006 |
| FR | 2874509 A1 | 3/2006 |
| GB | 828362 A | 2/1960 |
| WO | 9616718 A1 | 6/1996 |

* cited by examiner

SYSTEM FOR PROVIDING EMERGENCY OXYGEN AND THERAPEUTIC OXYGEN

CROSS-REFERENCE TO RELATED APPLICATIONS

This application is a national phase entry under 35 U.S.C. §371 of International Application No. PCT/EP2008/062774, filed Sep. 24, 2008, published in German, which claims the benefit of the filing date of U.S. Provisional Patent Application No. 60/998,781 filed Oct. 12, 2007, and of German Patent Application DE 10 2007 048 924.4 filed on Oct. 12, 2007, the disclosures of which are hereby incorporated herein by reference.

The invention relate to a system for providing emergency oxygen and therapeutic oxygen in an aircraft, a device for providing therapeutic oxygen, an aircraft with a system for providing emergency oxygen and therapeutic oxygen, and the use of a system for providing emergency oxygen and therapeutic oxygen in an aircraft.

Conventional devices for providing therapeutic oxygen are only provided at individual locations in the aircraft, if present at all, and are also most often designed as auxiliary, non-integrated components. As a result, conventional devices for providing therapeutic oxygen exhibit a highly restricted functionality or flexibility.

It is an object of the invention to indicate a device for providing therapeutic oxygen that has an elevated flexibility and user-friendliness.

This object is achieved by means of a system for providing emergency oxygen and therapeutic oxygen, a device for providing therapeutic oxygen, an aircraft with a system for providing emergency oxygen and therapeutic oxygen, and the use of a system for providing emergency oxygen and therapeutic oxygen in an aircraft.

An exemplary embodiment of the invention provides a system for providing emergency oxygen and therapeutic oxygen in an aircraft, having an oxygen source, an oxygen conduction system with a second oxygen outlet, a device for providing emergency oxygen with a second oxygen inlet, a device for providing therapeutic oxygen, having a first oxygen inlet and a first oxygen outlet, wherein the second oxygen outlet can be coupled with the first oxygen inlet, the first oxygen outlet can be coupled with the second oxygen inlet, and the second oxygen outlet can be coupled with the second oxygen inlet.

According to another exemplary embodiment of the invention a device for providing therapeutic oxygen is provided, having a first oxygen inlet and a first oxygen outlet, wherein an oxygen outlet of an oxygen conduction system can be coupled with the first oxygen inlet, the first oxygen outlet can be coupled with an oxygen inlet of a device for providing emergency oxygen, wherein the first oxygen inlet is looped internally relative to the first oxygen outlet, wherein the device for providing therapeutic oxygen has a first port for an application device, wherein the first port is designed for a predetermined flow rate.

According to another exemplary embodiment of the invention an aircraft is provided having a system for providing emergency oxygen and therapeutic oxygen with the features outlined above.

According to another exemplary embodiment of the invention a system for providing emergency oxygen and therapeutic oxygen with the features outlined above in an aircraft is provided.

The following definitions are used within the framework of the present patent application:

Emergency Oxygen:

Emergency oxygen is used in the aircraft in situations where it might no longer be possible to provide the passengers with an adequate oxygen supply by simply breathing in the cabin air. This may be characterized for a cabin pressure further reduced relative to the cabin pressure that prevails during normal flight operations, for example due to a leak or tear in the aircraft hull, so that the available partial oxygen pressure of the cabin air might no longer be sufficient for providing the passengers with an adequate oxygen supply. In such a case, emergency oxygen is applied, for example is provided via the automatic deployment of oxygen masks from the cabin ceiling or personal supply channel of the aircraft. The use of these emergency oxygen masks individually supplies the passengers with oxygen, so as to in this way ensure that the body of the respective passenger receives an adequate supply of oxygen overall.

Therapeutic Oxygen:

Therapeutic oxygen does not differ from emergency oxygen in terms of its physical characteristics, such as temperature and water saturation. As a result, therapeutic oxygen can also be provided from the same oxygen source as the emergency oxygen. Since the therapeutic oxygen is provided during routine operations, meaning at normal pressure conditions in the cabin, the pressure in the oxygen conduction system of the aircraft, and hence the flow rate of therapeutic oxygen, can be lower than the flow rate of emergency oxygen. Therapeutic is most often made available to the respective passenger based on a medical indication, where possible permanently throughout the entire flight, for example so as to make it easier for the passenger to breathe, or provide an elevated level of oxygen based on another medical indication.

Oxygen Source:

An oxygen source is any device that is suitable for providing pure or high-percentage oxygen in an aircraft.

Possible oxygen sources here include chemical oxygen generators, portable or permanently installed oxygen cylinders, or portable or permanently installed oxygen generators, so-called OBOGS.

Operating States:

References to two different operating states are made within the framework of the present description of the invention.

The first operating state is here characterized by the provision of emergency oxygen using the known emergency oxygen masks (or if therapeutic oxygen was provided to a passenger beforehand, by the application device for therapeutic oxygen used for this purpose) as indicated previously, for example given a pressure loss in the aircraft cabin. Therefore, the first operating state routinely represents an extraordinary emergency situation during flight.

The second operating state is characterized by providing therapeutic oxygen using an application device, for example a medical oxygen mask. Therefore, the second operating state does not represent any extraordinary operating state during flight, but is rather offered at the request of the passenger or based on a medical indication during regular flight operations.

As graphically shown in one exemplary embodiment of the invention, a system for providing emergency oxygen and therapeutic oxygen in an aircraft is created that makes it possible to flexibly and individually provide both emergency oxygen and therapeutic oxygen to a plurality or to all possible seats in an aircraft.

The use of a shared oxygen source for providing emergency oxygen and for providing therapeutic oxygen, and in particular the use of the same oxygen conduction system in the aircraft, make it possible to set up the system according to the invention much more easily, or even to easily retrofit or expand the latter after the fact.

In this case, the system according to the invention may be able to permit the provision of therapeutic oxygen to any seat in the aircraft, thereby eliminating any logistical problems that might arise during the assignment of seats, so that the requirement for therapeutic oxygen need no longer be taken into account during check-in.

Integrating the device for providing therapeutic oxygen into the personal supply channel (PSC) of an aircraft may additionally enable an optically not-invasive integration into the aircraft, thereby imparting a harmonious overall impression of the aircraft cabin, or one that need not be unnecessarily spoiled.

Therefore, the system according to the invention may be modular in design, so as to enable integration of the device for providing therapeutic oxygen during initial outfitting or tailored to individual flights, depending on what the airline requires. It may also be decided to only accommodate a few devices for providing therapeutic oxygen, which can be retrofitted and allocated based on need and current requirements.

Additional exemplary embodiments can be gleaned from the dependent claims.

Also described are embodiments of the system according to the invention for providing emergency oxygen and therapeutic oxygen. However, these embodiments also apply with respect to the device for providing therapeutic oxygen, the aircraft having a system for providing emergency oxygen and therapeutic oxygen, and the use of a system for providing emergency oxygen and therapeutic oxygen in an aircraft.

In another exemplary embodiment, the system for providing emergency oxygen and therapeutic oxygen may further have a device for providing therapeutic oxygen that exhibits a first port for an application device, wherein the first port is designed for a predetermined flow rate.

A corresponding port for an application device, for example a medical oxygen mask or a regular oxygen mask of the kind used for providing emergency oxygen in an aircraft, may enable a simple application of the therapeutic oxygen for the passenger in need.

The use of a first port with a first predetermined flow rate may further increase the simplicity and user-friendliness of the system according to the invention, since the flow rate need not be individually adjusted, thereby precluding a potential source of error.

The flow rate may here depend on a specific pressure in the oxygen conduction system during the application of therapeutic oxygen, or can essentially always provide a predetermined flow rate independently of the pressure in the oxygen conduction system.

In another exemplary embodiment of the system according to the invention for providing emergency oxygen and therapeutic oxygen, the device for providing therapeutic oxygen may have a second port for an application device, wherein the second port can be designed for a second predetermined flow rate.

A second port may make it possible to smoothly provide therapeutic oxygen to a second passenger in the same row of seats. The second predetermined flow rate can here be identical to the first predetermined flow rate, so that both passengers are provided with essentially the same amount of therapeutic oxygen, for example, or it may differ from the first predetermined flow rate.

However, it may be possible to supply two passengers with different flow rates, for example two liters per minute to one passenger and four liters per minute to another passenger, or one passenger can be individually provided with a currently advisable and/or medically indicated amount of therapeutic oxygen based upon his or her respective condition, needs or wishes.

In another exemplary embodiment of the system according to the invention for providing emergency oxygen and therapeutic oxygen, at least one of the first and second ports may be auto-activating.

An auto-activating port may here enable a flow of oxygen through the simple insertion of a part of the application device, for example a hose, without the latter having been separately activated at the port or on the device.

Therefore, an auto-activating may reduce or minimize the necessary individual steps for providing therapeutic oxygen. This makes it possible to preclude a potential source of error for the non-activation of a port when providing therapeutic oxygen.

In another exemplary embodiment of the system according to the invention for providing emergency oxygen and therapeutic oxygen, at least one of the devices for providing emergency oxygen and for providing therapeutic oxygen can be configured for incorporation into a personal supply channel of an aircraft.

A corresponding integration into the PSC may make it possible to offer a corresponding device for providing therapeutic oxygen individually for each row of seats.

Through incorporation into the PSC, the device for providing therapeutic oxygen may be integrated into the aircraft systems in such a way as to be able to integrate this device into the aircraft in a non-invasive manner. A flush installation in the PSC combined with the use of a cover flap, for example, makes it possible to completely hide the device for providing therapeutic oxygen when it is not needed, making it invisible.

This may make it possible to effectively avoid a situation where passengers become disconcerted by a device that stands out in the open, and is hence visible, and injuring themselves on it out of carelessness. In addition, passengers are also denied of any chance to independently activate the device, and damaging it in the worst-case scenario.

It may also be conceivable to incorporate a device according to the invention for providing therapeutic oxygen individually into the PSC, and hence into the aircraft, by means of quick-assembly couplings quick-coupling elements on the oxygen inlet or oxygen outlet for the short-term, e.g., for the usual time that an aircraft stands idle between two flights. For example, incorporating a device for providing therapeutic oxygen in this way makes it possible to use a predetermined space in the PSC, but one that is not occupied and hence is only provided with a dummy flap. As a result, a device according to the invention for providing therapeutic oxygen can be secured in any desired row of seats in an aircraft, but without having to do so when first equipping the aircraft. This may make it possible to individualize the aircraft interior equipment after the fact, or simply to adjust it to a specific, individual situation during a specially booked flight.

In another exemplary embodiment of the system according to the invention for providing emergency oxygen and therapeutic oxygen, the working pressure of the oxygen in the oxygen conduction system can be lower in a second operating state for the application of therapeutic oxygen than in a first operating state for the application of emergency oxygen, in particular lower than a triggering pressure with which the device for providing emergency oxygen can be activated.

This may make it possible to connect the device for providing therapeutic oxygen to the same conduction system as for the device used for providing emergency oxygen. However, the assembly and integration of the device for providing therapeutic oxygen can be greatly simplified, and may further be made significantly more cost effective.

A lower working pressure for the oxygen in the conduction system, for example 1 bar, within the framework of the second operating state can also preclude the random and unintended triggering of the device for providing emergency oxygen, for example the dropping down of emergency oxygen masks, which can require a significantly higher working pressure for the oxygen in the conduction system.

In another exemplary embodiment of the present invention, the device for providing therapeutic oxygen may have a regulator for setting a predetermined oxygen flow rate.

Such a regulator may make it possible to adjust the predetermined oxygen flow rate individually to the needs of a passenger for whom therapeutic oxygen is to be provided.

In addition, this may compensate for a pressure drop or pressure fluctuations in the oxygen conduction system, for example. It may also be conceivable, for example while providing several or even a plurality of passengers with therapeutic oxygen, to respond to a resultant altered load situation in the oxygen conduction system and compensate for the latter.

In addition, a passenger to be provided with therapeutic oxygen may individually adjust the predetermined oxygen flow rate to his or her overall condition. This ensures that a specific minimal oxygen flow rate (e.g., two liters per minute) is not dipped below, and that a specific maximum oxygen flow rate (e.g., four or even six liters per minute) is not exceeded.

In another exemplary embodiment of the present invention, the device for providing therapeutic oxygen may be set up to provide a predetermined emergency oxygen flow rate in the first operating state at the at least one port.

As a result, a situation in which the mask for providing therapeutic oxygen has to be switched for an emergency oxygen mask may be avoided, for example given a pressure drop in the cabin. This may ensure that the passenger is always provided with a sufficient amount of additional oxygen.

It is also conceivable for the predetermined emergency oxygen flow rate issued by the device for providing therapeutic oxygen in the first operating state to be higher than the regular emergency oxygen flow rate that would be issued by the device for providing emergency oxygen. This can reflect the amount of oxygen required by the passenger, which further exceeds the normal requirement during an emergency.

In another exemplary embodiment of the present invention, the system for providing emergency oxygen and therapeutic oxygen may also have a device for activating or deactivating the second operating state.

This device may be situated in a central or protected location on the aircraft, so as to ensure operation exclusively by the flight personnel, or it may be coupled with the auto-activation of a port of the device for providing therapeutic oxygen.

This may make it possible to prevent the oxygen conduction system from having a permanent supply pressure for providing therapeutic oxygen, without it even being required. As a result, unnecessary oxygen consumption or premature wear of the oxygen conduction system, e.g. on any gaskets present, may be avoided.

Embodiments of the device according to the invention for providing therapeutic oxygen are described below. However, these embodiments apply both to the system for providing emergency oxygen and therapeutic oxygen for the system having a system for providing emergency oxygen and therapeutic oxygen, and to the use of a system for providing emergency oxygen and therapeutic oxygen in an aircraft.

In an exemplary embodiment of the present invention, the device for providing therapeutic oxygen may further have a second port for an application device, the second port of which is designed for a second predetermined flow rate.

The second predetermined flow rate may here also be essentially identical to a first predetermined flow rate, or differ from the latter. This enables an application of two different flow rates depending on the circumstance, or two different passengers may be simultaneously supplied with therapeutic oxygen at the same or different flow rates.

In another exemplary embodiment of the present invention, at least one of the first port and second port may be auto-activating.

Auto-activating may here also be understood as automatic activation by plugging an application device into a port, thereby isolating the flow of oxygen.

In another exemplary embodiment of the present invention, the device for providing therapeutic oxygen may be designed for incorporation into a personal supply channel of an aircraft.

This may make it possible to place the device for providing therapeutic oxygen in an optically non-invasive location within the aircraft cabin, or to hide it from view when not needed.

In another exemplary embodiment of the present invention, the device for providing therapeutic oxygen may have a regulator for setting a predetermined oxygen flow rate.

The regulator may here act on at least one of the first port and second port, on both simultaneously, or differently as a function of the respective predetermined flow rates of the individual ports. A predetermined oxygen flow rate may also be set independently for the respective first and second ports.

In another exemplary embodiment of the invention, the device for providing therapeutic oxygen may be set up to provide a predetermined emergency oxygen flow rate to the at least one port in the first operating state.

This emergency oxygen flow rate may depend on an elevated supply pressure in the oxygen conduction system in the first operating state, and may further additionally depend on the first or second predetermined flow rate, in particular exceed the regular emergency oxygen supply flow rate by the latter.

While an expanded regulating option using the regulator for setting a predetermined oxygen flow rate may also be conceivable, the predetermined emergency oxygen flow rate as made available by the device for providing emergency oxygen cannot be dipped below.

In another exemplary embodiment of the invention, the device for providing therapeutic oxygen may further have a device for providing emergency oxygen, wherein the device for providing emergency oxygen has a second oxygen inlet that is connected or coupled with the first oxygen outlet.

This enables the creation of a compact, yet still modular device, which can be incorporated as a unit into the personal supply channel of an aircraft. As a result, both emergency oxygen and therapeutic oxygen can be provided at any seat in the aircraft.

Exemplary embodiments of the invention are shown in the following figures, and will be described in greater detail below.

Shown on.

The same or corresponding components in various figures are marked with identical reference numbers.

The depictions in the figures are diagrammatic and not to scale.

Drawing reference to FIG. 1, a system for providing emergency oxygen and therapeutic oxygen according to an exemplary embodiment of the present invention will be described below.

The system for providing emergency oxygen and therapeutic oxygen 1 has an oxygen source 10, to which the oxygen conduction system 20 is connected, which is below distributed throughout the aircraft.

To this end, the oxygen conduction system 20 branches in the aircraft, and has distributed second oxygen outlets 21. The second operating state is activated and deactivated via the device 11 only shown diagrammatically here. The device 11 can be manually operated by the aircraft personnel at a central location, or be coupled with the ports 43, 44.

The second oxygen outlet 21 is coupled with the first oxygen inlet 41 of the device for providing therapeutic oxygen 40.

The device for providing therapeutic oxygen 40 further has a first oxygen outlet 42, which is coupled with the second oxygen inlet 31 of the device for providing emergency oxygen 30.

In this case, the first oxygen inlet 41 is looped to the first oxygen outlet 42, and further branches off to the two ports 43 and 44. The branching, division and distribution coupled in particular with the measures for ensuring the respective predetermined flow rates of the ports 43, 44 are not shown in any greater detail on FIG. 1, but rather only as a diagrammatic distribution device 48.

Figure 1:
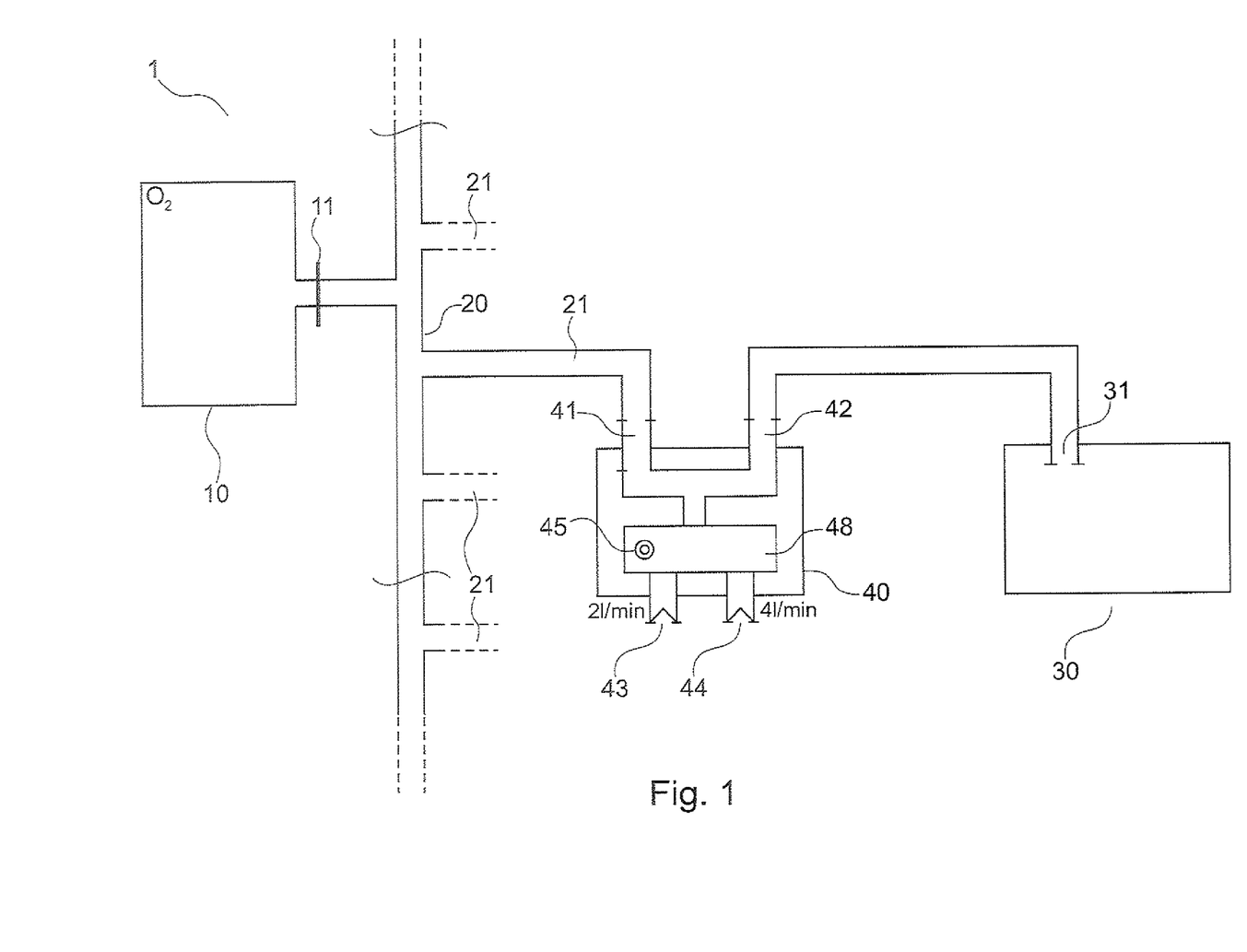
FIG. 1 is a diagrammatic view of the system for providing emergency oxygen and therapeutic oxygen.

In addition to the option depicted on FIG. 1, the looping through process can also take place in the distribution device 48 as a component thereof.

The device for providing therapeutic oxygen 40 further exhibits a regulator or controller 45, which makes it possible to set the first and/or second predetermined flow rate, whether together or individually.

In this case, the flow rate may be set manually, for example by means of a setting wheel, or the flow rate may be automatically regulated to a set desired value, for example by means of a pressure reducer.

The ports 43, 44 are designed for connecting a respective application device, for example a medical oxygen mask. As an example, FIG. 1 depicts the port 43 as a port with a predetermined flow rate of two liters of oxygen per minute, and the port 44 the a second predetermined flow rate of four liters of oxygen per minute.

This indication may in the following serve as a respective minimal predetermined flow rate for ports 43, 44, which can be increased by the regulator 45 up to a maximum possible value of six liters of oxygen per minute, for example (individually or combined). Other predetermined flow rates are conceivable.

Although not depicted on FIG. 1, the second oxygen outlet 21 can be directly connected to the second oxygen inlet 31, making it possible to completely decouple the device for providing therapeutic oxygen from the oxygen conduction system.

Also conceivable are check valves in the oxygen conduction system 20, which are not shown on FIG. 1.

Both the device for providing emergency oxygen 30 and the device for providing therapeutic oxygen 40 (not shown on FIG. 1) can be incorporated in a personal supply channel.

Figure 2:
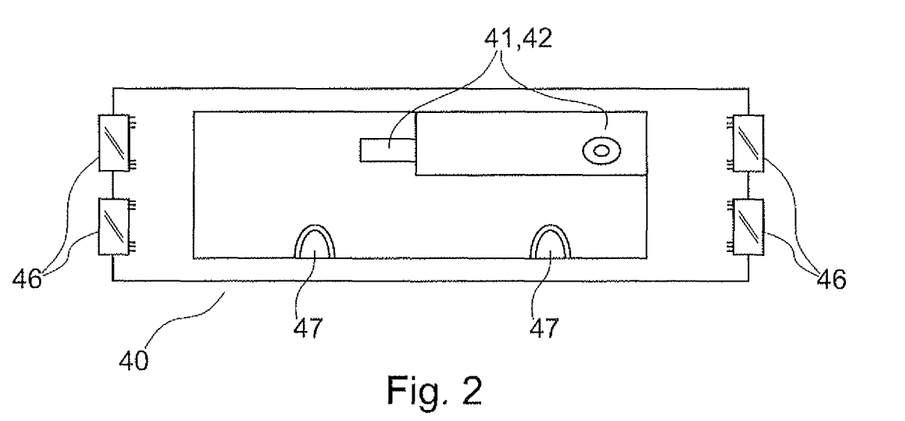
FIG. 2 is a rear view of the device for providing therapeutic oxygen.

FIG. 2 further presents a rear view of a device for providing therapeutic oxygen 40 is depicted.

The device here has a first oxygen inlet 41 and a second oxygen outlet 42, which can here be designed as pneumatic ports.

The pneumatic ports may here be designed as pressure-tight quick coupling ports, although a permanent connection is also possible, for example in the form of a hose band clip.

The device 40 further has a hose retainer 47, so that the oxygen conduction system, here comprised of compression-proof hoses, can be easily guided and installed without buckling.

In addition, the device for providing therapeutic oxygen 40 has quick assembly elements 46 of the kind conventionally used in devices incorporated into the PSC.

This may enable a quick or brief assembly and disassembly of the device 40, on the one hand to retrofit it during the time an aircraft stands idle, and on the other to easily and quickly dismantle it when being serviced.

Figure 3:
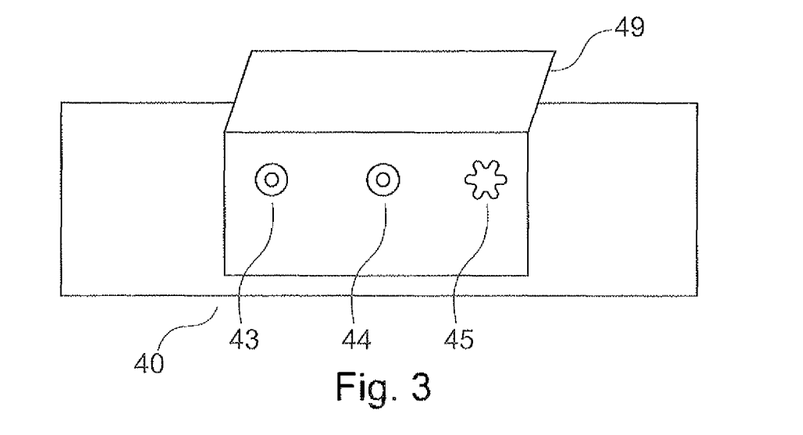
FIG. 3 is a front view of the device for providing therapeutic oxygen.

FIG. 3 presents a front view of the device according to the invention for providing therapeutic oxygen 40.

The device 40 here has a viewing flap 49, which when closed optically covers the individual elements of the device for providing therapeutic oxygen 40. The flap can be provided with a mechanism (not shown) to ensure that only aircraft personnel can open and close it. To this end, for example, use can be made of a special key, or the mechanism can be covered.

Situated under the flap 49 on FIG. 3 are ports 43, 44 for connecting a respective application device, for example a medical oxygen mask, as well as the regulator for setting a predetermined flow rate. The respectively set predetermined flow rate can be visualized via markings (not shown), or the use of a separate display (not shown here) is also conceivable.

Figure 4:
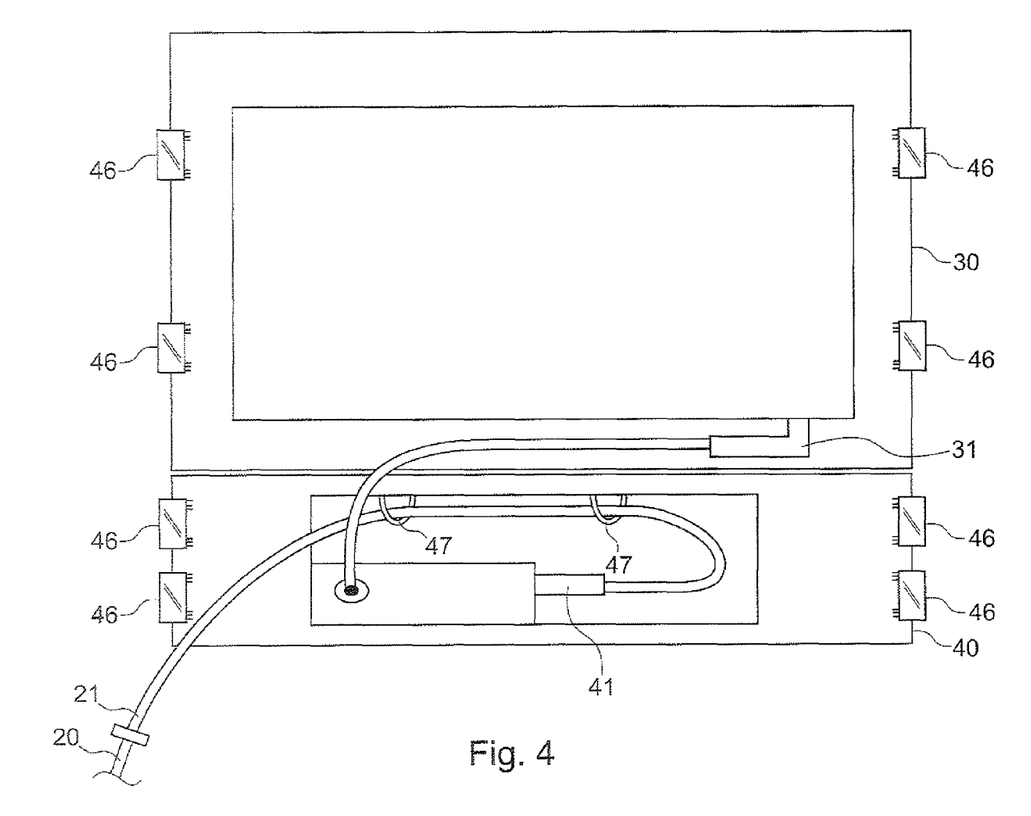
FIG. 4 is a combined view of the device for providing therapeutic oxygen and the device for providing emergency oxygen for arrangement in the PSC.

FIG. 4 presents a rear view shown the combination of a device for providing emergency oxygen 30 with a device for providing therapeutic oxygen 40.

The second oxygen outlet 21 of the oxygen conduction system 20, here taking the form of a hose held by the two hose retainers 47, is guided to the first oxygen inlet 41. The first oxygen outlet 42 is then coupled with the second oxygen inlet 31 of the device for providing emergency oxygen 30.

Both devices 30, 40 are attached in the PSC by means of the quick assembly elements 46. Three inches is a possible or conventional width for the side used to secure the quick assembly elements 46 for the device for providing therapeutic oxygen 40.

The embodiments of the invention are not restricted to the preferred embodiments depicted on the figures. Rather, a plurality of variants is conceivable, all making use of the described solution and principle according to the invention, even given fundamentally different types of embodiments.

Let it be noted that the principle according to the invention is not limited to aircraft, but can rather be applied in any means of transportation, in particular for trains, ships, buses, etc.

In addition, let it be noted that "has" or "comprises" do not preclude any other elements or steps, and that "an" or "a" do not rule out a plurality. Let it further be noted that features described with reference to one of the above exemplary embodiments can also be used in combination with other features of other exemplary embodiments described above. Reference numbers in the claims are not to be construed as restrictions.

REFERENCE LIST

1 System for providing emergency oxygen and therapeutic oxygen
10 Oxygen source
11 Device for activating/deactivating the second operating state
20 Oxygen conduction system
21 Second oxygen outlet
30 Device for providing emergency oxygen
31 Second oxygen inlet
40 Device for providing therapeutic oxygen
41 First oxygen inlet
42 First oxygen outlet
43 First port
44 Second port
45 Regulator
46 Quick assembly element
47 Hose retainer
48 Distribution device
49 Viewing flap

The invention claimed is:

1. A system for providing emergency oxygen and therapeutic oxygen in an aircraft, comprising:
   an oxygen source;
   an oxygen conduction system with a second oxygen outlet;
   a device for providing emergency oxygen with a second oxygen inlet;
   a device for providing therapeutic oxygen arranged between the second oxygen outlet and the device for providing emergency oxygen, comprising:
      a first oxygen inlet; and
      a first oxygen outlet;
      wherein the oxygen source is a shared oxygen source for providing both emergency oxygen and therapeutic oxygen using the same oxygen conduction system;
   wherein the second oxygen outlet of the conduction system is adapted to be coupled with the first oxygen inlet of the device for providing therapeutic oxygen,
   the first oxygen outlet of the device for providing therapeutic oxygen is adapted to be coupled with the second oxygen inlet of the device for providing emergency oxygen,
   wherein the device for providing therapeutic oxygen comprises a first port for an application device, wherein the first port is configured for a first predetermined flow rate;
   wherein the device for providing therapeutic oxygen comprises a second port for an application device, wherein the second port is configured for a second predetermined flow rate;
   wherein the second oxygen outlet of the conduction system is adapted to be coupled with the second oxygen inlet of the device for providing emergency oxygen and wherein the first oxygen inlet is looped internally to the first oxygen outlet
   wherein the device for providing emergency oxygen and the device for providing therapeutic oxygen are configured to be incorporated in a personal supply channel of an aircraft;
   wherein the system is adapted for a first operating state and a second operating state;
   wherein in the first operating state the system is configured to provide emergency oxygen;
   wherein in the second operating state the system is configured to provide therapeutic oxygen;
   wherein in the second operating state a working pressure of the oxygen in the oxygen conduction system is lower than a triggering pressure for activating the device for providing emergency oxygen; and
   wherein the device for providing therapeutic oxygen is configured to provide a predetermined emergency oxygen flow rate in the first operation state.

2. The system of claim 1,
   wherein at least one of the first port or the second port is auto-activating.

3. The system of claim 1,
   wherein a working pressure of oxygen in the oxygen conduction system is lower in the second operating state for the application of therapeutic oxygen than in the first operating state for the application of emergency oxygen.

4. The system of claim 1,
   wherein the device for providing therapeutic oxygen comprises a regulator or controller for setting a predetermined oxygen flow rate.

5. The system of claim 1,
   wherein the device for providing therapeutic oxygen is set up in such a way as to provide a predetermined emergency oxygen flow rate in the first operating state at at least one port.

6. The system of claim 1, further comprising
   a device for activating or deactivating the second operating state.

7. The system of claim 1, further comprising a first hose for coupling the second oxygen outlet of the oxygen conduction system to the first oxygen inlet of the device for providing therapeutic oxygen.

8. The system of claim 1, further comprising a second hose for coupling the first oxygen outlet of the device for providing therapeutic oxygen to the second oxygen inlet of the device for providing emergency oxygen.

9. The system of claim 1, further comprising a distribution device for distributing the oxygen flowing into the first oxygen outlet to at least one of the first port, the second port and the second oxygen inlet of the device for providing emergency oxygen.

10. An aircraft comprising:
   a system for providing emergency oxygen and therapeutic oxygen in an aircraft, comprising:
   an oxygen source;
   an oxygen conduction system with a second oxygen outlet;
   a device for providing emergency oxygen with a second oxygen inlet;
   a device for providing therapeutic oxygen arranged between the second oxygen outlet and the device for providing emergency oxygen and comprising:
      a first oxygen inlet; and
      a first oxygen outlet;
   wherein the oxygen source is a shared oxygen source for providing both emergency oxygen and therapeutic oxygen by using the same oxygen conduction system;
   wherein the second oxygen outlet of the conduction system is adapted to be coupled with the first oxygen inlet of device for providing therapeutic oxygen,
   the first oxygen outlet of the device for providing therapeutic oxygen is adapted to be coupled with the second oxygen inlet of the device for providing emergency oxygen, wherein the device for providing therapeutic oxygen comprising a first port for an application device, wherein the first port is configured for a first predetermined flow rate;

wherein the device for providing therapeutic oxygen comprising a second port for an application device, wherein the second port is configured for a second predetermined flow rate;

wherein the second oxygen outlet of the conduction system is adapted to be coupled with the second oxygen inlet of the device for providing emergency oxygen and wherein the first oxygen inlet is looped internally to the first oxygen outlet wherein the device for providing emergency oxygen and the device for providing therapeutic oxygen are configured to be incorporated in a personal supply channel of an aircraft;

wherein the system is adapted for a first operating state and a second operating state;

wherein in the first operating state the system is configured to provide emergency oxygen;

wherein in the second operating state the system is configured to provide therapeutic oxygen;

wherein in the second state a working pressure of the oxygen in the oxygen conduction system is lower than a triggering pressure for activating the device for providing emergency oxygen; and wherein the device for providing therapeutic oxygen is configured to provide a predetermined emergency oxygen flow rate in the first operation state.

* * * * *